United States Patent
Sher (10) Patent No.: US 10,058,529 B2
(45) Date of Patent: *Aug. 28, 2018

(54) NUTRACEUTICAL COMPOSITION FOR PDE4 INHIBITION, ENHANCED DOPAMINE METABOLISM AND LONG TERM POTENTIATION

(71) Applicant: Justin Sher, Woodside, CA (US)

(72) Inventor: Justin Sher, Woodside, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/081,787

(22) Filed: Mar. 25, 2016

(65) Prior Publication Data

US 2016/0213642 A1    Jul. 28, 2016

Related U.S. Application Data

(63) Continuation of application No. PCT/US2014/057923, filed on Sep. 27, 2014.

(60) Provisional application No. 62/047,055, filed on Sep. 7, 2014, provisional application No. 62/046,953, filed on Sep. 6, 2014, provisional application No. 61/883,433, filed on Sep. 27, 2013.

(51) Int. Cl.

| | |
|---|---|
| *A61K 31/352* | (2006.01) |
| *A61K 31/221* | (2006.01) |
| *A61K 31/353* | (2006.01) |
| *A61K 36/28* | (2006.01) |
| *A61K 31/198* | (2006.01) |
| *A61K 31/4415* | (2006.01) |
| *A61K 31/4525* | (2006.01) |
| *A61K 9/48* | (2006.01) |
| *A61K 45/06* | (2006.01) |
| *A61K 31/205* | (2006.01) |
| *A61K 31/216* | (2006.01) |
| *A61K 31/403* | (2006.01) |
| *A61K 31/675* | (2006.01) |
| *A61K 36/185* | (2006.01) |
| *A61K 36/53* | (2006.01) |
| *A23L 19/00* | (2016.01) |
| *A23L 33/105* | (2016.01) |
| *A23L 33/15* | (2016.01) |
| *A23L 33/175* | (2016.01) |

(52) U.S. Cl.
CPC ............ *A61K 31/352* (2013.01); *A23L 19/09* (2016.08); *A23L 33/105* (2016.08); *A23L 33/15* (2016.08); *A23L 33/175* (2016.08); *A61K 9/48* (2013.01); *A61K 9/485* (2013.01); *A61K 9/4858* (2013.01); *A61K 9/4866* (2013.01); *A61K 31/198* (2013.01); *A61K 31/205* (2013.01); *A61K 31/216* (2013.01); *A61K 31/221* (2013.01); *A61K 31/353* (2013.01); *A61K 31/403* (2013.01); *A61K 31/4415* (2013.01); *A61K 31/4525* (2013.01); *A61K 31/675* (2013.01); *A61K 36/185* (2013.01); *A61K 36/28* (2013.01); *A61K 36/53* (2013.01); *A61K 45/06* (2013.01); *A23V 2002/00* (2013.01)

(58) Field of Classification Search
CPC ................................................. A61K 31/352
See application file for complete search history.

(56) References Cited

U.S. PATENT DOCUMENTS

| | | | |
|---|---|---|---|
| 6,436,946 B1 | 8/2002 | Mann | |
| 8,029,830 B2 * | 10/2011 | Foley | A61K 31/352 424/702 |
| 9,149,457 B2 | 10/2015 | Sher | |
| 2008/0044390 A1 | 2/2008 | Jin | |
| 2009/0048339 A1 | 2/2009 | Kanwar | |
| 2011/0020443 A1 | 1/2011 | Liu | |
| 2011/0064712 A1 | 3/2011 | Amato | |
| 2011/0159048 A1 | 6/2011 | Crain | |
| 2011/0177097 A1 | 7/2011 | Shulman | |
| 2012/0041045 A1 | 2/2012 | Harvey | |
| 2012/0121743 A1 | 5/2012 | Garnier | |

FOREIGN PATENT DOCUMENTS

| | | |
|---|---|---|
| WO | 2007123609 A1 | 11/2007 |
| WO | 2007123699 A1 | 11/2007 |
| WO | 2006153426 A1 | 12/2008 |
| WO | 2008153426 A1 | 12/2008 |

OTHER PUBLICATIONS

Nootriment. "Countdown: The Top 5 Most Effective Nootropic Stacks." © 2016. Available from: < http://nootriment.com/most-effective-nootropic-stacks/ >.*

Norton, K.J. "Phytochemicals in Foods—15 Health Benefits of Resveratrol." (c) Feb. 2012. Available from: < http://womenhealth-phytochemicals.blogspot.tw/2012/02/phytochemicals-in-foods-15-health.html >.* de Souza, N.J., et al. "Forskolin: A Labdane Diterpenoid with Antihypertensive, Positive Inotropic, Platelet Aggregation Inhibitory, and Adenylate Cyclase Activating Properties." Medicinal Research Reviews. (1983), vol. 3, No. 2, pp. 201-219.*

Nice, Glenn. Purdue University. "Japanese Knotweed (*Polygonum cuspidatum*)." © Feb. 2007. Available from: < https://ag.purdue.edu/btny/weedscience/documents/japaneseknotweed07.pdf >.*

"Colchicum, Indian Herb." © Feb. 10, 2011. Available from: < https://web.archive.org/web/20110210124024/http://www.indianetzone.com/25/colchicum_indian_herb.htm >.*

(Continued)

*Primary Examiner* — Noble E Jarrell
*Assistant Examiner* — John S Kenyon
(74) *Attorney, Agent, or Firm* — Berliner & Associates (57) ABSTRACT

A nootropic combination for increasing cognitive functioning. The combination includes a phosphodiesterase 4 inhibitor and a cyclic adenosine monophosphate increasing agent. In some versions, the phosphodiesterase inhibitor is a flavonoid such as luteolin, and the cyclic adenosine monophosphate increasing agent is a labdane diterpene such as forskolin. The combination can also include one or a combination of L-phenylalanine, L-carnitine, acetyl-L-carnitine, and vitamin B6. In some versions, plant extracts, such as artichoke extract can be used as a source of the PDE4 inhibitor. Methods of using the combination to increase cognitive functioning are also included.

36 Claims, 3 Drawing Sheets

(56) References Cited

OTHER PUBLICATIONS

WebMD. "Resveratrol Supplements." © Mar. 5, 2012. Available from: < https://web.archive.org/web/20120305161408/http://www.webmd.com/heart-disease/resveratrol-supplements >.*
Dean, W. "Forskolin and cAMP." NaturoDoc. © Mar. 24, 2012. Available from: < https://web.archive.org/web/20120324190007/http://www.naturodoc.com/forskolin.htm >.*
WebMD. "Acetyl-L-Carnitine." © Mar. 5, 2011. Available from: < https://web.archive.org/web/20110305114337/http://www.webmd.com/vitamins-supplements/ingredientmono-834-acetyl-l-carnitine.aspx?activeingredientid=834&activeingredientname=acetyl-l-carnitine >.*
WebMD. "Phenylalanine." © Nov. 10, 2010. Available from: < https://web.archive.org/web/20101110034128/http://www.webmd.com/vitamins-supplements/ingredientmono-653-phenylalanine.aspx?activeingredientid=653&activeingredientname=phenylalanine >.*
Sahelian, R. "L-Carnitine supplement benefit and side effects, dosage of 250 mg, 500 mg, weight loss help?" © Apr. 22, 2012. Available from: < https://web.archive.org/web/20120422060956/http://www.raysahelian.com/carnitine.html >.*
Sheehan, J. "What Are the Benefits of Vitamin B6 to the Brain?" San Francisco Chronicle. © Feb. 24, 2013. Available from: < https://web.archive.org/web/20130224052851/http://healthyeating.sfgate.com/benefits-vitamin-b6-brain-4217.html >.*
Wattanathorn, J., et al. "Piperine, the potential functional food for mood and cognitive disorders." Food and Chemical Toxicology. (2008), vol. 46, pp. 3106-3110).*
Berge, S., et al. "Pharmaceutical Salts." J. Pharm. Sci. (Jan. 1977), vol. 66, No. 1, pp. 1-19.*
FYI Living. "Brain Function Improved by Luteolin in Celery, Parsley, Chamomile Tea." © Jun. 30, 2011. Available from: < https://fyiliving.com/diet/brain-function-improved-by-luteolin >.*
"Globe artichoke (Cynara scolymus L.)." © 2011. Available from: < http://www.naturesownherbs.com/ns/DisplayMonograph.asp?storeID=F541321FCA7A46F39570F4B746463119&DocID=bottomline-artichoke >.*
Bhatt, B. "Pharmaceutical Technology: Capsules." © Jul. 2007. Available from: < http://nsdl.niscair.res.in/jspui/bitstream/12356789/747/1/Revised%20CAPSULES.pdf >.*
Post #212 by "X_Danny_X" dated May 31, 2012—06:23 PM in www.longecity.org/forum/topic/51732-chemically-induced-ltp Re: Chemically induced LTP?
Post #253 by X_Danny_X dated Jun. 2, 2012—04:31 AM in www.longecity.org/forum/topic/51732-chemically-induced-ltp Re: Chemically induced LTP?
Post #257 by medievil dated Jun. 2, 2012—06:15 AM in www.longecity.org/forum/topic/51732-chemically-induced-ltp Re: Chemically induced LTP?
Post #297 by middpanther88 dated Jun. 8, 2012—02:07 AM in www.longecity.org/forum/topic/51732-chemically-induced-ltp Re: Chemically induced LTP?
Post #300 by trip96 dated Jun. 8, 2012—02:59 AM in www.longecity.org/forum/topic/51732-chemically-induced-ltp Re: Chemically induced LTP?
Post #315 by nupi dated Jun. 10, 2012—06:16 PM in www.longecity.org/forum/topic/51732-chemically-induced-ltp Re: Chemically induced LTP?
Post #377 X_by Danny_X dated Jun. 28, 2012—02:06 AM in www.longecity.org/forum/topic/51732-chemically-induced-ltp Re: Chemically induced LTP?
Post #458 by gbpackers dated Jul. 9, 2012—05:46 AM in www.longecity.org/forum/topic/51732-chemically-induced-ltp Re: Chemically induced LTP?
Post #460 by zrbarnes dated Jul. 19, 2012—08:53 AM in www.longecity.org/forum/topic/51732-chemically-induced-ltp Re: Chemically induced LTP?
Post #462 by gbpackers dated Jul. 19, 2012—03:56 PM in www.longecity.org/forum/topic/51732-chemically-induced-ltp Re: Chemically induced LTP?
Post #636 by IA87 dated Aug. 20, 2012—07:26 PM in www.longecity.org/forum/topic/51732-chemically-induced-ltp Re: Chemically induced LTP?
Post #638 by unbeatableking dated Aug. 20, 2012—07:57 PM in www.longecity.org/forum/topic/51732-chemically-induced-ltp Re: Chemically induced LTP?
Post #205 by "abelard lindsay" dated May 29, 2012—03:59 PM in www.longecity.org/forum/topic/51732-chemically-induced-ltp Re: Chemically induced LTP?
International Search Report re PCT/US2014/057923 dated Sep. 2, 2015.
K Rutten et al: Phosphodiesterase Inhibitors Enhance Object Memory Independent of Cerebral Blood Flow and Glucose Utilization in Rats; Neuropsychopharmacology (2009) 34, pp. 1914-1925.
T Egawa et al: Rolipram and Its Optical Isomers, Phosphodiesterase 4 Inhibitors, Attenuated the Scopolamine-Induced Impairments of Learning and Memory in Rats; Jpn. J. Pharmacol. 75, pp. 275-281 (1997).
HT Zhang et al: Effects of rolipram on scopolamine-induced impairment of working and reference memory in the radial-arm maze test in rats; Psychopharmacology (Berl). Jun. 2000; 150(3): pp. 311-316. Abstract Only.
HT Zhang et al: Inhibition of Cyclic AMP Phosphodiesterase (PDE4) Reverses Memory Deficits Associated with NMDA Receptor Antagonism; Neuropsythepharmacology 2000 vol. 23 No. 2, pp. 198-204.
HT Zhang et al: Effects of the novel PDE4 inhibitors MEM1018 and MEM1091 on memory in the radial-arm maze and inhibitory avoidance tests in rats; Psychopharmacology (Berl) May 2005;179(3):613-9, Epub Jan. 26, 2005 Abstract Only.
JH McLean et al: A phosphodiesterase inhibitor, cilomilast, enhances cAMP activity to restore conditioned odor preference memory after serotonergic depletion in the neonate rat; Neurobiol Learn Mem. Jul. 2009;92(1):pp. 63-69 doi: 10.1016/j.nlm.2009.02.003. Epub Feb. 20, 2009. Abstract Only.
C Wang et al: The phosphodiesterase-4 inhibitor rolipram reverses Aβ-induced congitive impairment and neuroinflammatory and apoptotic responses in rats; Int J Neuropsychopharmacol. Jul. 2012; 15(6):pp. 749-766. doi: 10.1017/S1461145711000836. Epub Jun. 9, 2011.Abstract Only
GM Rose et al: Phosphodiesterase inhibitors for congitive enhancement; Curr Pharm Des. 2005;11(26): pp. 3329-3334. Abstract Only.
J Drott et al: Etazolate improves performance in a foraging and homing task in aged rats; Eur J Pharmacol, May 25, 2010;634(1-3):pp. 95-400. doi: 10.1016/j.ejphar.2010,02.036. Epub Mar. 17, 2010.Abstact Only.
LX Li et al: Prevention of cerebral ischemia-induced memory deficits by inhibiton of phosphodiesterase-4 in rats; Metab Brain Dis. Mar. 2011;26(1);pp. 37-47. doi: 10.1007/s11011-011-9235-0. Epub Feb. 17, 2011 Abstract Only.
M Gallant et al: Discovery of MK-0952, a selective PDE4 inhibitor for the treatment of long-term memory loss and mild congnitive impairment; Bioorg Med Chem Lett. Nov. 15, 2010;20(22):pp. 6387-6393. doi. 10.1016/j.bmcl.2010.09.087. Eub Sep. 21, 2010. Abstract Only.
RJ Heaslip et al: Emetic, central nervous system, and pulmonary activities of rolipram in the dog, Eur J Pharmacol. Nov. 24, 1995;286(3):pp. 281-290, Abstract Only.
O Bruno et al: GEBR-7b, a novel PDE4D selective inhibitor that improves memory in rodents at non-emetic doses; British Journal of Pharmacology (2011) 164 pp. 2054-2063.
S Mackenzie et al: Action of rolipram on specific PDE4 cAMP phosphodiesterase isoforms and on the phosphorylation of cAMP-response-element-binding protein (CREB) and p38 mitogen-activated protein (MAP) kinase in U937 monocytic cells; Biochem. J. (2000) 347, pp. 571-578 (Printed in Great Britain).
W Xu et al: Individual CREB-target genes dictate usage of distinct cAMP-responsive coactivation mechanisms; EMBO J. Jun. 20, 2007; 26(12): pp. 2890-2903. Published online May 24, 2007. doi: 10.1038/sj.emboj.7601734.

(56) References Cited

OTHER PUBLICATIONS

E Benito et al: cAMP Response Element-Binding Protein Is a Primary Hub of Activity-Driven Neuronal Gene Expression; The Journal of Neuroscience, Dec. 14, 2011 • 31(50): pp. 18237-18250.
J Lee et al: Mitochondrial Cyclic AMP Response Element-binding Protein (CREB) Mediates Mitochondrial Gene Expression and Neuronal Survival; J Biol Chem. Dec. 9, 2005; 280(49): pp. 40398-40401. doi:10.1074/jbc. C500140200.
K Deisseroth et al: Signaling from Synapse to Nucleus: Postsynaptic CREB Phosphorylation during Multiple Forms of Hippocampal Synaptic Plasticity; Neuron, vol. 16, pp. 89-101, Jan. 1996.
S Kida: A Functional Role for CREB as a Positive Regulator of Memory Formation and LTP; Exp Neurobiol. Dec. 2012; 21(4): pp. 136-140.
A Suzuki et al: Behavioral/Systems/Cognitive Upregulation of CREB-Mediated Transcription Enhances Both Short-and Long-Term Memory; J. Neurosci., Jun. 15, 2011, 31(24): pp. 8786-8802.
HPT Ammon et al: Forskolin : From an Ayurvedic Remedy to a Modern Agent; Planta Medica 1985 pp. 473-477.
KB Sermon et al: Forskolin: a unique diterpene activator of cyclic AMP-generating systems; J Cyclic Nucleotide Res. 1981;7(4): pp. 201-224 Abstract Only.
M Barad et al: Rolipram, a type IV-specific phosphodiesterase inhibitor, facilitates the establishment of long-lasting long-term potentiation and improves memory; Proc. Natl. Acad. Sci. USA, vol. 95, pp. 15020-15025, Dec. 1998.
MC Yu et al: Luteolin, a non-selective competitive inhibitor of phosphodiesterases 1-5; displaced [3H]-rolipram from high-affinity rolipram binding sites and reversed xylazine/ketamine-induced anesthesia; Eur J Pharmacol. Feb. 2010;627(1-3): pp. 269-275 Abstract Only.
Al Chan et al: Inhibitory effects of quercetin derivatives on phosphodiesterase isozymes and high-affinity [(3) H]-rolipram binding in guinea pig tissues; Invest New Drugs, Oct. 2008;26(5): pp. 417-424 Abstract Only.
L Yang et al: Hesperidin-3-O-Methylether is More Potent than Hesperidin in Phosphodiesterase Inhibition and Suppression of Ovalbumin-Induced Airway Hyperresponsiveness; Evidence-Based Complementary and Alternative Medicine, vol. 2012, Article ID 908562, 12 pages.
S-J Park et al: Resveratrol Ameliorates Aging-Related Metabolic Phenotypes by Inhibiting cAMP Phosphodiesterases; Cell. Feb. 3, 2012; 148(3): pp. 421-433.
W-C Ko et al: Biochanin A, a Phytoestrogenic Isoflavone with Selective Inhibition of Phosphodiesterase 4, Suppresses Ovalbumin-Induced Airway Hyperresponsiveness; Evidence-Based Complementary and Alternative Medicine, vol. 2011, Article ID 635058, 13 pages.
MR Nichols et al: Tyrosine kinase-independent inhibition of cyclic-AMP phosphodiesterase by genistein and tyrphostin 51; Arch Biochem Biophys, Jun. 15, 1999;366(2): pp. 224-230 Abstract Only.
Al Harvey et al: Pharmacological actions of the South African medicinal and functional food plant *Sceletium tortuosum* and its principal alkaloids; J Ethnopharmacol. Oct. 11, 2011;137(3): pp. 1124-1129 Abstract Only.
JE Brown et al: Luteolin-rich artichoke extract protects low density lipoprotein from oxidation in vitro; Free Radio Res. Sep. 1998;29(3):pp. 247-255 Abstract Only.
MC Yu et al: Luteolin, a non-selective competitive inhibitor of phosphodiesterases 1-5, displaced [3H]-rolipram from high-affinity rolipram binding sites and reversed xylazine/ketamine-induced anesthesia; Eur J Pharmacol. Feb. 10, 2010;627(1-3):pp. 269-275 (Epub Oct. 22, 2009) Abstract Only.
Y Kitagawa et al: Prediction and validation of a mechanism to control the threshold for inhibitory synaptic plasticity; Molecular Systems Biology 5:280 (2009); pp. 1-16.

D Puzzo at al: Role of phosphodiesterase 5 in synaptic plasticity and memory; Neuropsychiatric Disease and Treatment 2008:4(2) pp. 371-387.
N Otmakhov et al: Forskolin-Induced LTP in the CA1 Hippocampal Region Is NMDA Receptor Dependent; J Neurophysiol 91:1955-1962, 2004 (First published Dec. 31, 2003).
KM Piech-Dumas: CREB mediates the cAMP-responsiveness of the tyrosine hydroxylase gene: use of an antisense RNA strategy to produce CREB-deficient PC12 cell lines; Brain Res Mol Brain Res. Jul. 5, 1999;70(2): pp. 219-230 Abstract Only.
SC Kumer et al: Intricate regulation of tyrosine hydroxylase activity and gene expression, J Neurochem. Aug. 1996;67(2):pp. 443-462 Abstract Only.
A Slominski et al: L-tyrosine and L-DOPA as hormone-like regulators of melanocytes functions; Pigment Cell Melanoma Res. Jan. 2012 ; 25(1): pp. 14-27.
A Amadasi et al: Pyridoxal 5'—phosphate enzymes as targets for therapeutic agents; Curr Med Chem. 2007;14(12): pp. 1291-1324 Abstract Only.
BF Curtin et al: Forskolin, an inducer of cAMP, up-regulates acetylcholinesterase expression and protects against organophosphate exposure in neuro 2A cells; Mol Cell Biochem. Oct. 2006;290(1-2):pp. 23-32 (Epub Aug. 19, 2006) Abstract Only.
P Hartvig et al: Reversal of postoperative somnolence using a two-rate infusion of physostigmine; Acta Anaesthesiol Scand. Nov. 1989;33(8):pp. 681-385.
HL White et al: Acetyl-L-carnitine as a precursor of acetylcholine Neurochem Res. Jun. 1990;15(6):pp. 597-601 Abstract Only.
JH Chung: Metabolic benefits of inhibiting cAMP-PDEs with resveratrol; Adipocyte 1:4, pp. 256-258; Oct./Nov./Dec. 2012.
RH,Alasbahi et al: Forskolin and derivatives as tools for studying the roie of cAMP; Pharmazie. Jan. 2012;67(1): pp. 5-13 Abstract Only.
DE Matthews: An Overview of Phenylalanine and Tyrosine Kinetics in Humans; J Nutr. Jun. 2007; 137(6 Suppl 1): pp. 1549S-1575S.
HC Lichtstein et al: Function of the vitamin B6 group: pyridoxal phosphate (codecarboxylase) in transamination: J Biol Chem. 161 (1): pp. 311-320.
PJ Rani et al: Protective efficacy of L-carnitine on acetylcholinesterase activity in aged rat brain; J Gerontal A Bioi Sci Med Sci. Mar. 2001;56(3) pp. B 140-B 141 Abstract Only.
RF Villa et al: ATP-ases of synaptic plasma membranes in striatum:Enzymatic systems for synapses functionality by in vivo administration of 1-acetylcamitine in relation to Parkinson's Disease; Neuroscience. Jun. 25, 2013;248C:pp. 414-426. [Epub ahead of print] Abstract Only.
B Gong et al: Persistent improvement in synaptic and cognitive functions in an Alzheimer mouse model after rolipram treatment; J Clin Invest. Dec. 2004;114(11):pp. 1624-1634.
P Voisin et al: Cyclic AMP-dependent regulation of tyrosine hydroxylase mRNA and immunofluorescence levels in rat retinal precursor cells: Cell Tissue Res. May 2013;352(2): pp. 207-216 (Epub Jan. 26, 2013) Abstract Only.
Post #1510 by "chung_pao" dated May 7, 2013—08:16 PM in www.longecity.org/forum/topic/51732-chemically-induced-ltp Re: Chemically induced LTP?
Post #1526 by "chung_pao" dated May 11, 2013—02:55 PM in www.longecity.org/forum/topic/51732-chemically-induced-ltp Re: Chemically induced LTP?
Post #1616 by "chung_pao" dated Jun. 27, 2013—11:39 PM in www.longecity.org/forum/topic/51732-chemically-induced-ltp Re: Chemically induced LTP?
Post #1653 by "chung_pao" dated Jul. 6, 2013—03:22 PM in www.longecity.org/forum/topic/51732-chemically-induced-ltp Re: Chemically induced LTP?
Post #1665 by "chung_pao" dated Jul. 11, 2013—02:37 AM in www.longecity.org/forum/topic/51732-chemically-induced-ltp Re: Chemically induced LTP?
Post #1667 by "chung_pao" dated May 7, 2013—08:16 PM in www.longecity.org/forum/topic/51732-chemically-induced-ltp Re: Chemically induced LTP?

(56) References Cited

OTHER PUBLICATIONS

Post #1728 by "chung_pao" dated Jul. 30, 2013—07:47 PM in www.longecity.org/forum/topic/51732-chemically-induced-ltp Re: Chemically induced LTP?
Post #1897 by "chung_pao" dated Sep. 14, 2013—10:16 PM in www.longecity.org/forum/topic/51732-chemically-induced-ltp Re: Chemically induced LTP?
Post #2173 by "chung_pao" dated Nov. 28, 2013—02:56 PM in www.longecity.org/forum/topic/51732-chemically-induced-ltp Re: Chemically induced LTP?
JH McLean et al: A phosphodiesterase inhibitor, cilomilast, enhances cAMP activity to restore conditioned odor preference memory after serotonergic depletion in the neonate rat; Neurobiol Learn Mem. Jul. 2009;92(1):pp. 63-69. doi: 10.1016/j.nlm.2009.02.003. Epub Feb. 20, 2009. Abstract Only.
Post #1 by abelard lindsay dated #1 as updated and edited on Mar. 14, 2013, Apr. 9, 2013, Jun. 13, 2013, Jun. 21, 2013, Jun. 27, 2013, Sep. 10, 2013, Oct. 2, 2013, Nov. 24, 2013, and Mar. 12, 2014, and edited by abelard lindsay on Mar. 14, 2014—03:22 PM in www.longecity.org/forum/topic/51732-chemically-induced-ltp Re: Chemically induced LTP?
Post #75 by health_nutty dated May 10, 2012—05:31 PM in www.longecity.org/forum/topic/51732-chemically-induced-ltp Re: Chemically induced LTP?
Post #121 by "abelard iindsay" dated May 20, 2012—07:27 PM in www.longecity.org/forum/topic/51732-chemically-induced-ltp Re: Chemically induced LTP?
Post #173 by "vali" dated May 25, 2012—01:15 AM in www.longecity.org/forum/topic/51732-chemically-induced-ltp Re: Chemically induced LTP?
Post #176 by "abelard lindsay" dated May 25, 2012—09:12 AM in www.longecity.org/forum/topic/51732-chemically-induced-ltp Re: Chemically induced LTP?
Post #195 by "ansatz22" dated May 28, 2012—08:25 PM in www.longecity.org/forum/topic/51732-chemically-induced-ltp Re: Chemically induced LTP?
Post #196 by "abelard lindsay" dated May 28, 2012—09:27 PM in www.longecity.org/forum/topic/51732-chemically-induced-ltp Re: Chemically induced LTP?
Post #197 zrbarnes dated Posted May 26, 2012—09:35 PM in www.longecity.org/forum/topic/51732-chemically-induced-ltp Re: Chemically induced LTP?
Post #205 by "abelard lindsay" dated Nov. 28, 2013—02:56 PM in www.longecity.org/forum/topic/51732-chemically-induced-ltp Re: Chemically induced LTP?
Post #212 by "X_Danny_X" dated May 31, 2012—08:23 PM.
Post #253 by X_Danny_X Jun. 2, 2012—04:31 AM.
257 medievil Jun. 2, 2012—06:15 AM.
297 middpanther88 Jun. 8, 2012—02:07 AM.
300 trip96 Jun. 8, 2012—02:59 AM.
315 nupi Jun. 10, 2012—06:16 PM.
377 X_Danny_X Jun. 28, 2012—02:06 AM.
458 gbpackers Jul. 9, 2012—05:46 AM
46 f 2 #460 zrbarnes Jul. 19, 2012—08:53 AM.
462 gbpackers Jul. 19, 2012—03:56 PM.
636 IA87 Aug. 20, 2012—07:26 PM.
638 unbeatableking Aug. 20, 2012—07:57 PM.
CREB From Wikipedia, the free enciyopedia, retrieved Sep. 26, 2012 5:44 AM from http://en.wikipedia.org/wiki/CREB.
Forskolin-Induced LTP in the CA1 Hippocampal Region is NMDA Receptor Dependent Nikolai Otmakhov, Lena Khibnik, Nonna Otmakhova, Stephen Carpenter, Shervin Riahi, Brent Asrican, John Lisman: Journal of Neurophysiology Published May 1, 2004 vol. 91 No. 5, 1955-1962 DOI: 10.1152.jn.00941.2003.
Long-term potentiation (neuroscience) from Wikipedia, the free encylopedia, retrieved Aug. 26, 2014, 8:25 AM from http://en.wikipedia.org/wiki/Long_term_potentiation.
Nutraceutical From Wikipedia, the free encyclopedia, retrieved Sep. 26, 2012 5:53 AM from http://en.wikipedia.org/wiki/Nutraceutical.
K Shimoi et al: Intestinal absorption of luteolin and luteolin 7-O-beta-glucoside in rats and humans. FEBS Lett. 1998; 438(3):220-4.
SM Wittemer et al: Bioavailability and pharmacokinetics of caffeoylquinic acids and flavonoids after oral administration of Artichoke leaf extracts in humans. Phytomedicine. 2005; 12(1-2):28-38.
A Perez et al: The flavonoid quercetin induces acute vasodilator effects in healthy volunteers: Correlation with beta-glucuronidase activity. Pharmacol Res. 2014; 89C:11-18.
K Shimoi et al: Deglucuronidation of a flavonoid, luteolin monoglucuronide, during inflammation, Drug Metab Dispos. 2001; (12):1521-4.
SP Lin et al: Pharmacokinetics and tissue distribution of resveratrol, emodin and their metabolites after intake of Polygonum cuspidatum in rats. J Ethnopharmacol. 2012;;144(3):671-6.
Y Kawai: β-Glucuronidase activity and mitochondrial dysfunction: the sites where flavonoid glucuronides act as anti-inflammatory agents. J Clin Biochem Nutr. 2014, 54(3):145-50.
O Tohyama et al: Klotho is a novel beta-glucuronidase capable of hydrolyzing steroid beta-glucuronides. J Biol Chem. 2004; 279(11):9777-84.
G Shoba et al: Influence of piperine on the pharmacokinetics of curcumin in animals and human volunteers. Planta Med. 1998; 64(4):353-6.
JJ Johnson et al. Enhancing the bioavailability of resveratrol by combining it with piperine. Mol Nutr Food Res. 2011; 55(8)1169-76.
Post #1142 on LONGECITY: Bioscience, Health & Nutrition: Brain Health by "jadamgo" Feb. 7, 2013—06:40 AM retrieved from http://www.longecity.org/forum/topic/51732-chemically-induced-ltp/page-39#entry 564700.
Post #1173 on LONGECITY: Bioscience, Health & Nutrition: Brain Health by "jadamgo" Feb. 12, 2013—07:38 PM downloaded from http://www.longecity.org/forum/topic/51732-chemially-induced-ltp/page-40#entry566063.
Post #59 on LONGECITY: Bioscience, Health & Nutrition: Brain Health by "abelard lindsay" May 5, 2012—01:37 PM retrieved from http://www.longecity.org/forum/topic/51732-chemically-induced/ltp/page-2#entry513884.
Post #862 on LONGECITY: Bioscience, Health & Nutrition: Brain Health by "zrbarns" Oct. 12, 2012—03:47 PM retrieved from http://www.longecity.org/forum/topic/51732-chemically-induced-ltp/page-29#entry539892.
Post #2165 on LONGECITY: Bioscience, Health & Nutrition: Brain Health by "magta39" Nov. 26, 2013—08:25 PM retrieved from http://www.longecity.org/forum/topic/51732-chemicaly-induced-ltp/page-73#entry626025.
Post #1464 on LONGECITY: Bioscience, Health & Nutrition: Brain Health by "chung_Pao" Apr. 23, 2013—06:52 PM retrieved from http://www.longecity.org/forum/topic/51732-chemically-induced-ltp/page-49#entry 581824.
Post on Slate Star Codex by "Scott Alexander" entitled "Nootropics Survey Results and Analysis" Feb 16, 2014 on Slate Star Codex retrieved from http://slatestarcodex.com/2014/02/16/nootropics-survey-results-and-analysis.
CILTEP White Paper by "Abelard Lindsay" copyright 2013 by Natureal Stacks LLC, retrieved from https://www.upgradedself.com/files/ciltep-white-paper.pdf.
Mar. 19, 2015 Office Action in Inventor's U.S. Appl. No. 14/499,143.

* cited by examiner

NUTRACEUTICAL COMPOSITION FOR PDE4 INHIBITION, ENHANCED DOPAMINE METABOLISM AND LONG TERM POTENTIATION

CROSS-REFERENCE TO RELATED APPLICATIONS

This application is a continuation of PCT Patent Application PCT/US2014/057923 filed on Sep. 27, 2014, which claims the benefit of U.S. Provisional Patent Applications 61/883,433 filed on Sep. 27, 2013, 62/046,953 filed on Sep. 6, 2014, and 62/047,055 filed on Sep. 7, 2014; the entire disclosures of all said applications are hereby incorporated by reference for all purposes.

BACKGROUND

Field of the Invention

The invention relates to nutritional supplements and methods of use thereof.

Related Art

There has been a significant amount of research into the benefits of PDE4 inhibitors. In animal models synthetic PDE4 inhibitors have been shown to enhance object memory, and to reverse deficits to learning, working and reference memory induced by scopolamine, NMDA antagonists and under conditions of depleted tryptophan and serotonin (references 1-6).

Several articles have been published in the literature that discuss the potential of PDE4 inhibitors for cognitive enhancement in those with Alzheimer's disease, dementia, and other neurodegenerative conditions. PDE4 inhibitors have also provided improvements in performance to aged animal brains and have been shown, in animal models, to provide protection from damage from certain types of ischemic strokes. Experimental new PDE4 inhibitors are regularly being developed with the intention of treating long-term memory loss and mild cognitive impairment. Unfortunately, one of the most studied PDE4 inhibitors, rolipram, has had the side effect of emesis (vomiting) at low doses. Much work remains for developing memory enhancing PDE4 inhibitors with better side-effect profiles than rolipram (references 7-13).

SUMMARY

In one aspect, a nootropic combination for increasing cognitive functioning in a human, or other mammal, is provided. The combination includes effective amounts of a phosphodiesterase 4 (PDE4) inhibitor and a cyclic adenosine monophosphate (cAMP) increasing agent. In embodiments of the nootropic combination: a) the combination includes an effective amount of acetyl-L-carnitine or a physiologically acceptable salt thereof; b) the PDE4 inhibitor includes a flavonoid, an alkaloid, or a stilbenoid, or any combination thereof; c) the PDE4 inhibitor includes luteolin, quercetin, hesperidin, biochanin A, genistein, mesembrenone, or resveratrol, or a glycoside thereof, a physiologically acceptable salt thereof, or any combination thereof; d) the cAMP increasing agent is a labdane diterpene; e) the cAMP increasing agent is forskolin, a glycoside thereof, or a physiologically acceptable salt thereof; f) when the cAMP increasing agent is forskolin, the forskolin is in a range of about 0.9 mg to about 4.4 mg per daily dose of the combination; g) when the cAMP increasing agent is forskolin, the ratio of acetyl-L-carnitine to forskolin is about 200:1 by weight; h) the combination further includes effective amounts of one or any combination of components selected from the group consisting of L-phenylalanine, L-carnitine, acetyl-L-carnitine, vitamin B6, and a physiologically acceptable salt thereof; i) the PDE4 inhibitor, the cAMP increasing agent, or both, can be added to the combination in the form of one or more plant extracts; j) the combination can be a nutritional supplement; or k) any combination of a)-j).

In a particular embodiment, the nootropic combination in capsule form includes, per capsule: about 300 mg of artichoke extract standardized to 5% cynarin; about 4/3 mg of forskolin; about 250 mg of acetyl-L-carnitine; about 500/3 mg of L-phenylalanine; and about 5/3 mg vitamin B6.

In another aspect, a nutritional supplement for increasing cognitive functioning in a human, or other mammal, is provided. The nutritional supplement includes effective amounts of forskolin and acetyl-L-carnitine, and further includes a plant extract including an effective amount of a PDE4 inhibitor. In embodiments of the nutritional supplement: a) the ratio of acetyl-L-carnitine to forskolin is about 200:1 by weight; b) the forskolin is in a range of about 0.9 mg to about 4.4 mg per daily dose of the supplement; c) the PDE4 inhibitor includes a flavonoid, an alkaloid, or a stilbenoid, or any combination thereof; d) the PDE4 inhibitor includes luteolin, quercetin, hesperidin, biochanin A, genistein, mesembrenone, or resveratrol, or a glycoside thereof, a physiologically acceptable salt thereof, or any combination thereof; e) the forskolin can be added to the nutritional supplement in the form of a *Coleus forskohlii* extract; or f) any combination of a)-e).

In a further embodiment, a method of increasing cognitive functioning in a human or other mammalian subject in need thereof is provided. The method includes administering any of the nootropic combinations for increasing cognitive functioning described in this application, including any of the nutritional supplements. Thus, in some embodiments, the method includes administering to the subject a nutritional supplement that includes effective amounts of a cyclic adenosine monophosphate (cAMP) increasing agent and acetyl-L-carnitine, and further includes a plant extract that includes an effective amount of a PDE4 inhibitor. In embodiments of the method: a) the cAMP increasing agent is forskolin, a glycoside thereof, or a physiologically acceptable salt thereof; b) the PDE4 inhibitor includes a flavonoid, an alkaloid, or a stilbenoid, or any combination thereof; c) the PDE4 inhibitor includes luteolin, quercetin, hesperidin, biochanin A, genistein, mesembrenone, or resveratrol, or a glycoside thereof, a physiologically acceptable salt thereof, or any combination thereof; d) the cAMP increasing agent is forskolin; e) when the nootropic combination includes forskolin, the ratio of acetyl-L-carnitine to forskolin is about 200:1 by weight; or f) when the nootropic combination includes forskolin, the forskolin can be added to the nutritional supplement in the form of a *Coleus forskohlii* extract; or g) any combination of a)-f).

In another aspect, a nutritional supplement for increasing cognitive functioning in a human, or other mammal, is provided. The nutritional supplement includes effective amounts of a phosphodiesterase 4 (PDE4) inhibiting flavonoid and a cyclic adenosine monophosphate (cAMP) increasing labdane diterpene. In some embodiments: a) the flavonoid can be luteolin, a glycoside thereof, or a physiologically acceptable salt thereof; b) the nutritional supplement can include artichoke extract as a source of the flavonoid; c) the labdane diterpene can be forskolin, a glycoside thereof, or a physiologically acceptable salt thereof; d) the nutritional supplement can further include effective amounts of one or any combination of components selected from the group consisting of L-phenylalanine, L-carnitine, acetyl-L-carnitine, vitamin B6, and piperine, and a physiologically acceptable salt thereof; or e) any combination of a)-d).

In some embodiments, the nutritional supplement includes in daily dosage form about 202.5 mg to about 990 mg of artichoke extract standardized to 5% cynarin, and about 0.9 mg to about 4.4 mg of forskolin. In some embodiments: a) the nutritional supplement further includes one or any combination of components selected from the group consisting of about 180 mg to about 880 mg of acetyl-L-carnitine per daily dosage of the nutritional supplement, about 112.5 mg to about 550 mg of L-phenylalanine per daily dosage of the nutritional supplement, about 2.25 mg to about 11 mg of vitamin B6 per daily dosage of the nutritional supplement, and about 10 mg to about 20 mg of piperine per daily dosage of the nutritional supplement; b) in embodiments containing acetyl-L-carnitine, the ratio of acetyl-L-carnitine to forskolin can be about 200:1 by weight; c) particular embodiments of the nutritional supplement can include about 180 mg to about 880 mg of acetyl-L-carnitine per daily dosage of the nutritional supplement; about 112.5 mg to about 550 mg of L-phenylalanine per daily dosage of the nutritional supplement; about 2.25 mg to about 11 mg of vitamin B6 per daily dosage of the nutritional supplement; or d) any combination of a)-c). In a particular embodiment, the nutritional supplement comprises, per daily dosage: about 900 mg of artichoke extract standardized to 5% cynarin; about 4 mg of forskolin; about 750 mg of acetyl-L-carnitine; about 500 mg of L-phenylalanine; and about 5 mg vitamin B6.

In a further aspect, a method of increasing cognitive functioning in a human or other mammalian subject in need thereof is provided. The method includes administering to the subject a nutritional supplement that includes therapeutically effective amounts of a phosphodiesterase 4 (PDE4) inhibiting flavonoid and a cyclic adenosine monophosphate (cAMP) increasing labdane diterpene. In some embodiments: a) the flavonoid can be luteolin, a glycoside thereof, or a physiologically acceptable salt thereof; b) the nutritional supplement can include artichoke extract as a source of the flavonoid; c) the labdane diterpene can be forskolin, a glycoside thereof, or a physiologically acceptable salt thereof; d) the nutritional supplement can further include therapeutically effective amounts of one or any combination of components selected from the group consisting of L-phenylalanine, L-carnitine, acetyl-L-carnitine, vitamin B6, and piperine, and a physiologically acceptable salt thereof; or e) any combination of a)-d).

In some embodiments, the method includes administering to the subject a nutritional supplement that includes in daily dosage form about 202.5 mg to about 990 mg of artichoke extract standardized to 5% cynarin, and about 0.9 mg to about 4.4 mg of forskolin. In some embodiments: a) the nutritional supplement further includes one or any combination of components selected from the group consisting of about 180 mg to about 880 mg of acetyl-L-carnitine per daily dosage of the nutritional supplement, about 112.5 mg to about 550 mg of L-phenylalanine per daily dosage of the nutritional supplement, about 2.25 mg to about 11 mg of vitamin B6 per daily dosage of the nutritional supplement, and about 10 mg to about 20 mg of piperine per daily dosage of the nutritional supplement; b) in embodiments containing acetyl-L-carnitine, the ratio of acetyl-L-carnitine to forskolin can be about 200:1 by weight; c) particular embodiments of the nutritional supplement can include about 180 mg to about 880 mg of acetyl-L-carnitine per daily dosage of the nutritional supplement; about 112.5 mg to about 550 mg of L-phenylalanine per daily dosage of the nutritional supplement; and about 2.25 mg to about 11 mg of vitamin B6 per daily dosage of the nutritional supplement; or d) any combination of a)-c). In a particular embodiment, the nutritional supplement comprises, per daily dosage: about 900 mg of artichoke extract standardized to 5% cynarin; about 4 mg of forskolin; about 750 mg of acetyl-L-carnitine; about 500 mg of L-phenylalanine; and about 5 mg vitamin B6.

In a further aspect, a nutritional supplement for increasing cognitive functioning in a human, or other mammal, is provided. The nutritional supplement includes an effective amount of means for inhibiting phosphodiesterase 4 (PDE4), an effective amount of means for increasing cyclic adenosine monophosphate (cAMP), and an effective amount of means for increasing acetylcholine. In some embodiments, the nutritional supplement also includes effective amounts of one or any combination of components selected from the group consisting of L-phenylalanine, L-carnitine, vitamin B6, and piperine.

In another aspect, a method of increasing cognitive functioning in a human or other mammalian subject in need thereof is provided. The method includes administering to the subject a nutritional supplement that includes therapeutically effective amounts of means for inhibiting phosphodiesterase 4 (PDE4), means for increasing cyclic adenosine monophosphate (cAMP), and means for increasing acetylcholine. In some embodiments, the nutritional supplement also includes effective amounts of one or any combination of components selected from the group consisting of L-phenylalanine, L-carnitine, vitamin B6, and piperine.

In another aspect, a nutritional supplement for increasing cognitive functioning in a human, or other mammal, is provided. The nutritional supplement includes effective amounts of mesembrenone, a glycoside thereof, or a physiologically acceptable salt thereof, and a cyclic adenosine monophosphate (cAMP) increasing labdane diterpene is provided. In some embodiments: a) the labdane diterpene can be forskolin, a glycoside thereof, or a physiologically acceptable salt thereof; b) the nutritional supplement can further include effective amounts of one or any combination of components selected from the group consisting of L-phenylalanine, L-carnitine, acetyl-L-carnitine, vitamin B6, and piperine, and a physiologically acceptable salt thereof; or c) any combination of a)-b).

BRIEF DESCRIPTION OF THE DRAWINGS

For a more complete understanding of the present invention, reference is now made to the following descriptions taken in conjunction with the accompanying drawings, in which.

DETAILED DESCRIPTION

Postings on a Longecity forum started by the inventor under the name "Abelard Lindsay" on Sep. 26, 2011, and including postings at least up to Sep. 27, 2013, are incorporated by reference herein. The Longecity forum can be accessed on the World Wide Web at: longecity.org/forum/topic/51732-chemically-induced-ltp.

In one aspect, a nootropic combination for increasing cognitive functioning is provided, comprising effective amounts of a phosphodiesterase 4 (PDE4) inhibitor and a cyclic adenosine monophosphate (cAMP) increasing agent. PDE4 inhibitors and cAMP increasing agents can be natural or synthetic. Examples of PDE4 inhibitors include, but are not limited to, theophylline, isobutylmethylxanthine, rolipram, and benzamide derivatives of rolipram. PDE4 inhibitors found in plant extracts include, but are not limited to, PDE4 inhibiting flavonoids, alkaloids, and stilbenoids. Phosphodiesterase 4 is a member of a family of phosphodiesterase enzymes that degrade 3',5'-cyclic nucleotides including cAMP. In humans, phosphodiesterase 4 is abundant in brain tissue.

Figure 1:
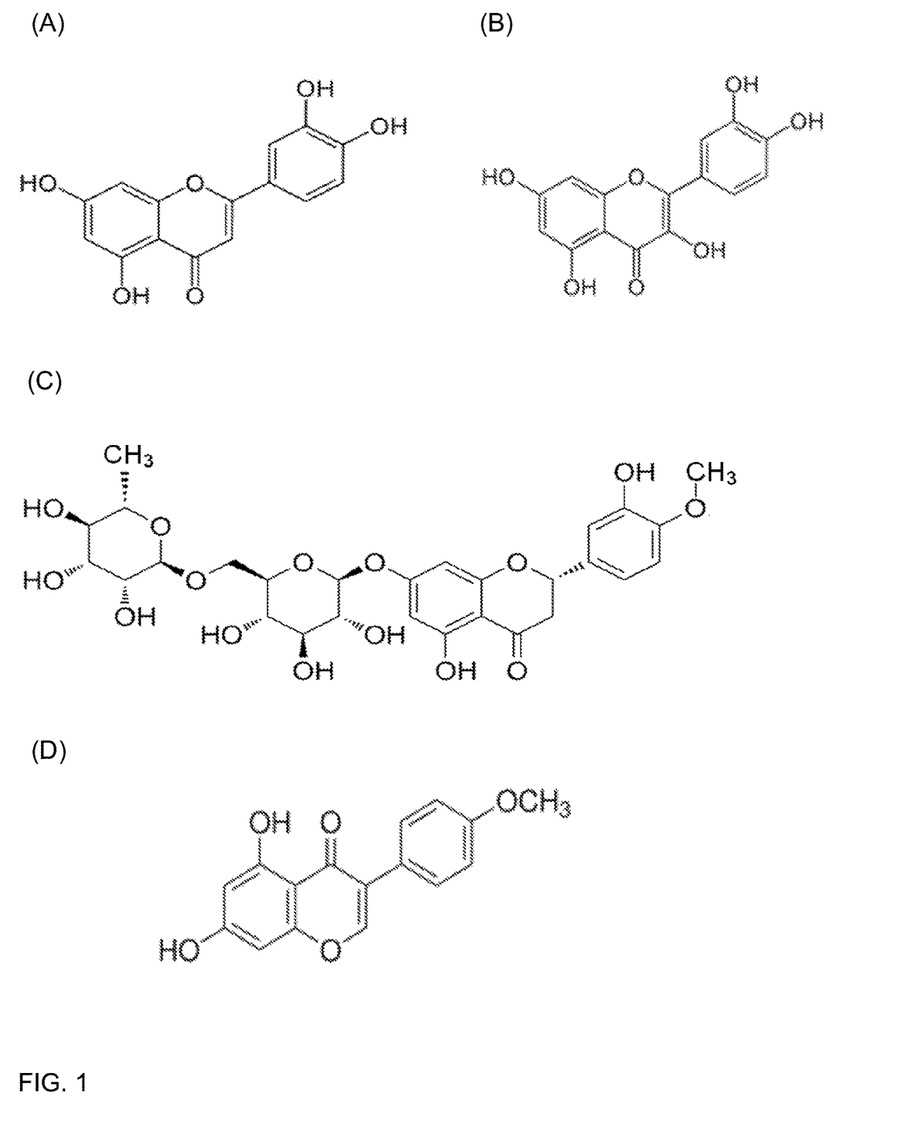
FIG. 1 is a panel showing the chemical structures of various compounds.

A flavonoid is a plant compound having a three ring backbone structure, including flavonoid glycosides. Luteolin, shown in FIG. 1A, is a flavonoid that can inhibit 3',5'-cyclic nucleotide phosphodiesterase enzymes, including PDE4. Luteolin is found in certain plants such as artichoke (*Cynara scolymus*), and artichoke extracts containing luteolin are commercially available. An artichoke extract can be standardized based upon the amount of cynarin, a caffeoylquinic acid present in artichoke. Other examples of PDE4 inhibiting flavonoids include, but are not limited to, quercetin (FIG. 1B) found in many plants including onion (*Allium cepa*), hesperidin (FIG. 1C) found in citrus plants, biochanin A (FIG. 1D) found in many plants including red clover (*Trifoleum pretense*), and genistein (FIG. 1E) found in soy beans. Extracts containing these plant compounds are commercially available. A non-limiting example of a PDE4 inhibiting alkaloid is mesembrenone shown in FIG. 1F. Mesembrenone is found in the succulent herb *Sceletium tortuosum*, also known as kanna, and kanna extracts containing mesembrenone are commercially available. Stilbenoids are stilbene derivatives having a C6-C2-C6 structure. A non-limiting example of a PDE4 inhibiting stilbenoid is resveratrol (FIG. 1G) found in grapes and other fruits. Grape extracts containing resveratrol are commercially available. Glycosides of luteolin, quercetin, hesperidin, biochanin A, genistein, mesembrenone, and resveratrol may also act as PDE4 inhibitors (references 46-51). PDE inhibitors are commercially available as purified components, for example, from Sigma-Aldrich Corp., St. Louis, Mo., USA, and/or as plant extracts from, for example, Now Foods, Bloomingdale, Ill., USA, Jarrow Formulas, Los Angeles, Calif., USA, Source Naturals, Scotts Valley, Calif., USA, Neutraceutical, Park City, Utah, USA, Swanson Health Products, Fargo, N. Dak., USA, Planetary Herbals, Soquel, Calif., USA, and Better Body Sports, Ventura, Calif., USA.

Agents that increase intracellular cAMP levels include, but are not limited to, hormones and other bioactive agents such as dopamine, isoproterenol, adenosine, carbacyclin, endothelin, epinephrine, glucagon, parathyroid hormone, prostaglandin, vasopressin, cholera toxin, pertussis toxin, and cAMP increasing labdane diterpenes. A labdane diterpene is a natural product having a bicyclic diterpene backbone structure. Forskolin, shown in FIG. 1H, is a labdane diterpene that can stimulate the enzyme adenylyl cyclase, which catalyzes the conversion of ATP to cAMP. Forskolin is found in the plant *Coleus forskohlii*, and *Coleus forskohlii* extracts containing forskolin are commercially available. Purified forskolin preparations are also commercially available. Synthetic and natural derivatives of forskolin, including but not limited to forskolin glycosides, 7-deacetylforskolin and 6-aminoacylforskolins, can stimulate adenylyl cyclase activity. In some embodiments, forskolin in the amount of about 1 to about 4 mg per daily dosage, or an amount of a forskolin derivative or other cAMP increasing agent producing an effect on cognitive functioning equivalent to about 1 to about 4 mg of forskolin per daily dosage, is included in the nootropic combination.

In some embodiments, the PDE4 inhibitor, the cAMP increasing agent, or both, can be added to the nootropic combination in the form of one or more plant extracts. For example, a nootropic combination can contain artichoke extract as a source of the PDE4 inhibitor luteolin and *Coleus forskohlii* extract as the source of forskolin. Plant extracts that can be used as sources of PDE4 inhibitors include, but are not limited to, onion, citrus, red clover and soy bean, or any combination thereof, as described above.

Cyclic AMP appears to play a role in long term potentiation and other nervous system processes. Combining an adenylyl cyclase stimulator with a PDE4 inhibitor can lead to enhanced cAMP production with decreased cAMP degradation, resulting in increased levels of cAMP in the body and increased intracellular cAMP levels. Thus, embodiments of the nootropic combination, including nutritional supplements, can affect nervous system functioning when administered to a subject.

In some embodiments, the nootropic combination includes physiologically acceptable or pharmaceutically acceptable salts of a PDE4 inhibitor, a cAMP increasing agent, and/or other components of the combination. Physiologically acceptable salts and pharmaceutically acceptable salts are well known in the art and include salts prepared from pharmaceutically acceptable non-toxic acids, including inorganic acids and organic acids. Suitable non-toxic acids can include inorganic and organic acids such as acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, hydrochloric, hydrobromic, phosphoric, sulfuric acids, and the like. Salts formed with, for example, a free carboxy group of an amino acid, can be derived from inorganic bases including, but not limited to, sodium, potassium, ammonium, calcium or ferric hydroxides, and organic bases including, but not limited to, isopropylamine, trimethylamine, histidine, and procaine.

The nootropic combination, or any individual components of the nootropic combination, can be taken orally in the form of a capsule, pill or tablet, for example, and can contain pharmaceutically or physiologically acceptable carriers. For example, inert, pharmaceutically or physiologically acceptable solid carriers can be one or more substances which may also act as diluents, flavoring agents, colorizers, solubilizers, lubricants, suspending agents, or binders. The solid carrier material can also include encapsulating material. Examples of carriers include, but are not limited to. inert diluents, such as calcium carbonate, sodium carbonate, sodium citrate, lactose, calcium phosphate, sodium phosphate, microcrystalline cellulose, corn starch, potato starch, and cellulose esters such as cellulose acetate, ethyl cellulose; granulating and disintegrating agents, for example, corn starch, or alginic acid, or complex silicates; binding agents, for example starch, polyvinylpyrrolidone, PEG-8000, gelatin or gum acacia, and lubricating agents, for example magnesium stearate, stearic acid, sodium lauryl sulfate, or talc.

Although oral administration of the nootropic combination or any of its components is the preferred route of administration, other means of administration such as intravenous, nasal or rectal administration, or by injection or inhalation, are also contemplated. Depending on the intended mode of administration, the combination or any of its components may be in the form of solid, semi-solid or liquid dosage forms, such as, for example, liquids, suspensions, suppositories, or powders. In some embodiments, the nootropic combination can be administered in unit dosage form suitable for single administration of a precise dosage. One skilled in this art may further formulate the composition or any of its components in an appropriate manner, and in accordance with accepted practices, such as those disclosed in Remington's Pharmaceutical Sciences, Gennaro, Ed., Mack Publishing Co., Easton, Pa. 1990.

The effective amount of the nootropic combination and any of its components can vary according to, for example, the weight of the subject administered to, the mode of administration, and the general health of the subject. The dose or effective amount will be ascertainable by one skilled in the art using known techniques (for example, see Ansel, et al., Pharmaceutical Dosage Forms and Drug Delivery; Lieberman (1992) Pharmaceutical Dosage Forms (vols. 1-3), Dekker, ISBN 0824770846, 082476918X, 0824712692, 0824716981; and Lloyd (1999) The Art, Science and Technology of Pharmaceutical Compounding).

In some embodiments, the nootropic combination can be administered simultaneously or sequentially and in any order. For example, the PDE4 inhibitor, the cAMP increasing agent, and other components of the combination can be administered as a combination simultaneously or sequentially in any order, depending on the embodiment.

The nootropic combination can be in a form to be administered as a single preparation, such as a capsule or tablet, and can be in a daily dosage form. In some embodiments, the combination is a nutritional supplement.

The nootropic combination can be administered to a subject to increase or enhance cognitive functioning Cognitive functioning refers to higher-order brain processes such as concentration, alertness, focus, attention, motivation, wakefulness, and long-term memory. An effective amount, or a therapeutically effective amount, of a substance is an amount that increases or enhances cognitive functioning in the subject.

In some cases, cognitive functioning can be assessed using cognitive tests such as long-term recall of studied material, spatial search and grammatical reasoning tests.

The subject can be a human or other mammal.

The primary means by which PDE4 inhibitors are theorized to improve learning and memory is by lengthening the duration during which the secondary messenger cyclic-adenosine monophosphate (cAMP) is present in cells, where it can activate the cAMP response element binding protein CREB and thus increase CREB's gene transcription activities in the nucleus and mitochondria. These gene transcription activities are what are theorized to lead to long term potentiation (LTP) activity which is crucial to learning and memory. Additionally, increased transcription of brain-derived neurotrophic factor (BDNF) by CREB has been linked to improved short-term memory in studies (references 14-20).

Forskolin is a chemical derived from the plant *Coleus forskohlii* which has been widely used in traditional Ayurvedic medicine. It has also has been extensively studied due to its ability to increase levels of intracellular cAMP (references 21-23).

Luteolin can inhibit the family of phosphodiesterase enzymes (PDE 1 through 5) that degrade 3',5'-cyclic nucleotides. Inhibition of phosphodiesterase 1 and phosphodiesterase 5 have both shown beneficial activity with regard to synaptic plasticity (references 24-27). PDE 4 specific inhibitors are also known, such as rolipram (reference 28).

CREB's activities in the cell have been shown to increase the transcription of enzymes which are key enzymes in dopamine metabolism, such as tyrosine hydroxylase. Increased transcription of these enzymes leads to increased processing of dopamine precursors. The essential amino acid L-phenylalanine is converted into L-tyrosine by phenylalanine hydroxylase and then converted into L-dopa by tyrosine hydroxylase. Vitamin B6 can support the conversion of L-dopa to dopamine by dopa decarboxylase (references 29-32). Thus, L-phenylalanine and/or Vitamin B6 can be added to embodiments of the nutritional supplement.

Some embodiments of the nootropic combination may lead to afternoon sleepiness and a temporary decrease in short term memory. Studies have provided evidence that forskolin increases transcription of the enzyme acetylcholinesterase. Acetylcholinesterase breaks down acetylcholine in the brain. Sleepiness is a common symptom of medicines that are anti-cholinergic so it would follow that excess acetylcholinesterase could lead to lower acetylcholine levels and thus sleepiness. Acetyl-L-carnitine has been shown to increase the levels of acetylcholine in the brain and thus could be helpful in counteracting increased transcription of acetylcholinesterase by forskolin (references 33-35). Thus, acetyl-L-carnitine, or L-carnitine, can be added to the nutritional supplement. In embodiments containing acetyl-L-carnitine or L-carnitine, afternoon drowsiness and short-term memory issues can be largely mitigated.

Kanna extract and mesembrenone have been shown to significantly inhibit PDE4 (reference 38). Embodiments containing kanna extract were effective at increasing cognitive functioning, although less beneficial than artichoke extract.

In particular embodiments, multiple components are combined to create a synergistic combination for improving synaptic and cognitive functions in the mammalian brain. These components include: a cyclic adenosine monophosphate (cAMP) increasing labdane diterpene such as forskolin; a PDE4 inhibiting flavonoid such as Luteolin contained within artichoke extract; the amino acid L-phenylalanine; vitamin B6; and the quaternary ammonium compound L-carnitine or its acylated derivative acetyl-L-carnitine.

Figure 2:
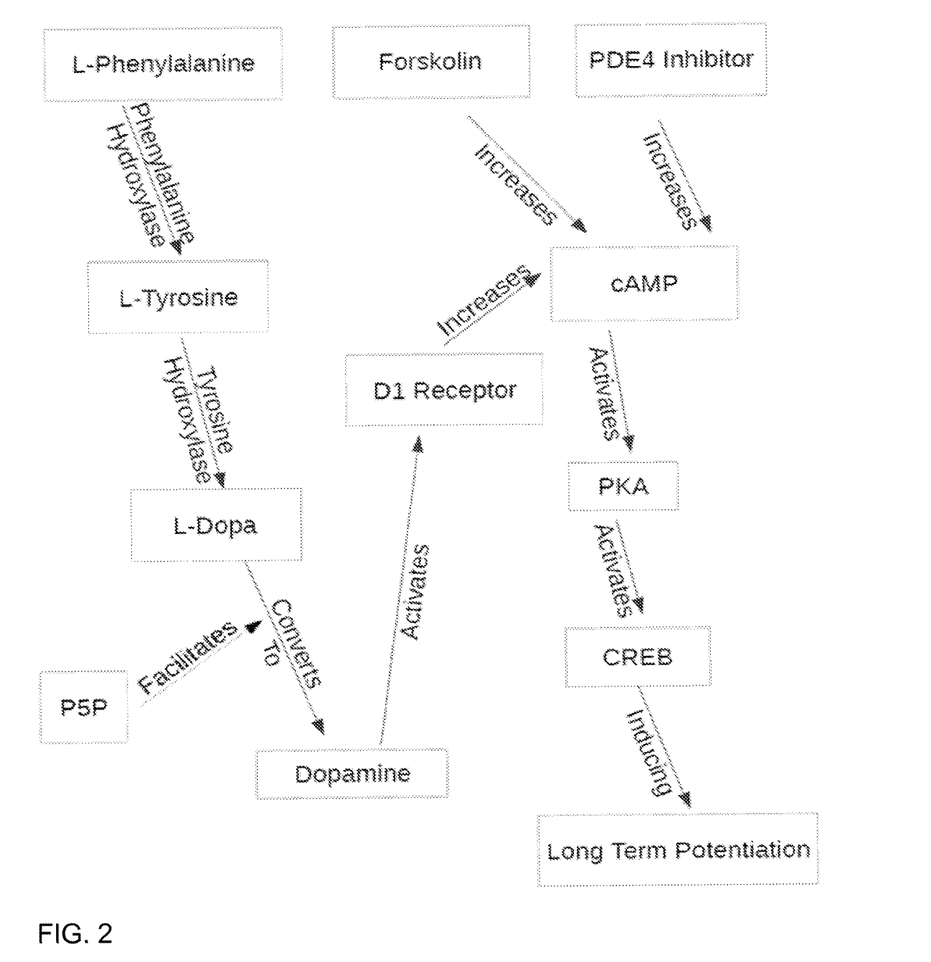
FIG. 2 is a diagram showing suggested interactions of components of a nutritional supplement.

Although not wishing to be bound by theory, it is believed that when these components are taken together orally in the form of a nutritional supplement, PDE-4 is inhibited and cAMP is increased leading to sustained activation of CREB (cAMP response element binding protein), which helps to maintain effective long-term potentiation (LTP) and thus memory. In addition, L-phenylalanine is believed to provide adequate precursors to the dopaminergic metabolic pathway to accommodate upregulation of tyrosine hydroxylase by PDE4 inhibition, and vitamin B6 is believed to behave as a dopamine metabolic co-factor (see FIG. 2). Also, L-carnitine and acetyl-L-carnitine are believed to counteract the upregulation of acetylcholinesterase caused by forskolin. Thus, it is believed that the dopamine co-factors provide a steady supply of co-factors to the enhanced D1/PKA/DARPP-32 signaling cascade caused by PDE-4 inhibition and the subsequent increase in dopamine synthesis and turnover due to increases in tyrosine hydroxylase gene transcription (references 36-45).

Some particular embodiments for an adult human that have been determined through experimentation include:
200 mg acetyl-L-carnitine;
1 mg forskolin;
225 mg artichoke extract standardized to 5% cynarin;
125 mg L-phenylalanine; and
2.5 mg vitamin B6.
Alternative formulas include:
200 mg acetyl-L-carnitine
1 mg forskolin
225 mg artichoke extract standardized to 5% cynarin;
or
1 mg forskolin
225 mg artichoke extract standardized to 5% cynarin
125 mg L-phenylalanine These particular embodiments are exemplary and the weight of each ingredient may be varied by 10% without significant degradation of efficacy. Also, from 1 to 2, 1 to 3, 1 to 4, 2 to 3, 2 to 4, 3 to 4, or 1, 2, 3 or 4 doses may be taken per day. Thus, in some embodiments, the range of ingredients per daily dosage can be:

about 202.5 mg to about 495 mg, about 202.5 mg to about 742.5 mg, or about 202.5 mg to about 990 mg artichoke extract standardized to 5% cynarin; and about 0.9 mg to about 2.2 mg, about 0.9 mg to about 3.3 mg, or about 0.9 mg to about 4.4 mg forskolin.

Alternatively, the daily dosage can be about 225 mg, about 450 mg, about 675 mg or about 900 mg artichoke extract standardized to 5% cynarin; and about 1 mg, about 2 mg, about 3 mg, or about 4 mg forskolin, or can be varied by 10% of such amounts.

Further, in some embodiments, the nutritional supplement can include one or a combination of the following ingredients, in ranges per daily dosage:

about 180 mg to about 440 mg, about 180 mg to about 660 mg, or about 180 mg to about 880 mg acetyl-L-carnitine;

about 112.5 mg to about 275 mg, about 112.5 mg to about 412.5 mg, or about 112.5 mg to about 550 mg L-phenylalanine; and about 2.25 mg to about 5.5 mg, about 2.25 mg to about 8.25 mg, or about 2.25 mg to about 11 mg vitamin B6.

Alternatively, the daily dosage can be about 200 mg, about 400 mg, about 600 mg, or about 800 mg acetyl-L-carnitine; about 125 mg, about 250 mg, about 375 mg, or about 500 mg L-phenylalanine; and about 2.5 mg, about 5 mg, about 7.5 mg, or about 10 mg vitamin B6, or can be varied by 10% of such amounts.

The alkaloid piperine (FIG. 1I) can also be included as a component of the nootropic combination, including the nutritional supplement. Piperine is present in black pepper and has been used in nutritional products to enhance the bioavailability of flavonoids by blocking glucuronidation in the liver and digestive tract. Piperine has been found to enhance the bioavailability of curcumin by 2000%, and enhance the bioavailability of resveratrol (references 52-53). In embodiments of the nutritional supplement, piperine can be included in the range of about 10 mg to about 20 mg per daily dose of the nootropic combination.

Additional inactive ingredients such as different types of color, filler, binder, capsule, and coating are permissible.

In embodiments containing acetyl-L-carnitine, a ratio of acetyl-L-carnitine to forskolin of about 200:1 by weight appears to provide particularly good effects on cognitive functioning.

Forskolin in the amount of 1-4 mg per daily dosage is less than the amount typically provided in forskolin supplements (25 mg to 50 mg). The 1-4 mg daily dosage was found by the inventor to provide positive cognitive benefits, while larger amounts produced side effects and diminished or eliminated cognitive benefits.

As used herein, the term "about" in reference to an amount of a substance indicates an amount within experimental error.

It is to be understood that the ranges and limits mentioned herein include all sub-ranges located within the prescribed limits, inclusive of the limits themselves unless otherwise stated.

The present invention may be better understood by referring to the accompanying examples, which are intended for illustration purposes only and should not in any sense be construed as limiting the scope of the invention.

Example 1

Artichoke Extract and Forskolin

The inventor ingested 900 mg artichoke extract standardized to 5% cynarin (Now Foods, Bloomingdale, Ill.) and 385 mg *Coleus forskohlii* root standardized to 1% forskolin yielding 3.85 mg forskolin (Neutraceutical, Park City, Utah). The combination was administered once per morning. After taking the combination, the inventor performed better on spatial search and grammatical reasoning tests compared to baseline. The inventor felt increased motivation and could study for longer periods of time. He also had subjectively better recall of material that was studied. The inventor experienced excessive tiredness in the afternoon, and short term memory, as measured by a paired-associate-learning test "Paired Associates" (Cambridge Brain Sciences, Ontario, Canada) in which a pair of items is learned (an object and its location), was slightly negatively affected.

Example 2

Artichoke Extract, Forskolin and L-Phenylalanine

The inventor ingested artichoke extract and forskolin as in Example 1, and also ingested up to 1500 mg L-Phenylalanine (Now Foods, Bloomingdale, Ill.). The combination was administered once per morning After taking the combination, the inventor performed better on spatial search and grammatical reasoning tests compared to baseline, felt increased motivation, could study for longer periods of time, and had subjectively better recall of material that was studied. Compared to the combination containing just artichoke extract and forskolin, the inventor experienced less tiredness in the afternoon. Short term memory, as measured by the paired-associate-learning test "Paired Associates" (Cambridge Brain Sciences, Ontario, Canada), was slightly negatively affected.

Example 3

Artichoke Extract, Forskolin, L-Phenylalanine and Vitamin B6

The inventor ingested artichoke extract, forskolin and L-phenylalanine as in Example 2, and also ingested 5 mg vitamin B6 as part of a B vitamin complex (Neutraceutical, Park City, Utah). The combination was administered once per morning After taking the combination, the inventor performed better on spatial search and grammatical reasoning tests compared to baseline, felt increased motivation, could study for longer periods of time, and had subjectively better recall of material that was studied. The inventor experienced less tiredness in the afternoon and the effects of the stack did not diminish over several days of taking it. Short term memory, as measured by the paired-associate-learning test "Paired Associates" (Cambridge Brain Sciences, Ontario, Canada), was slightly negatively affected.

Example 4

Artichoke Extract, Forskolin, L-Phenylalanine, Vitamin B6 and Acetyl-L-Carnitine The inventor ingested artichoke extract, forskolin, L-phenylalanine and vitamin B6 as in Example 3, and also ingested 750 mg of acetyl-L-carnitine (Primaforce, Burlington, N.C.). The combination was administered once per morning After taking the combination, the inventor performed better on spatial search and grammatical reasoning tests compared to baseline, felt increased motivation, could study for longer periods of time, and had subjectively better recall of material that was studied. The inventor experienced no tiredness in the afternoon. The amount of acetyl-L-carnitine relative to forskolin was increased until the inventor's paired associates scores no longer fell after taking the combination.

Example 5

This example is based on a testimonial by a subject. The subject was a female with concentration and memory problems. The nutritional supplement was in capsular form, with a capsule including 300 mg artichoke extract standardized to 5% cynarin, ~4/3 mg forskolin, 167 mg L-phenylalanine, 5/3 mg vitamin B6, and 250 mg acetyl-L-carnitine. Also included were cellulose, vegetable stearate and silica as carriers. After taking the nutritional supplement, the subject reported increased focus, energy and memory.

Example 6

This example is based on a testimonial by a male subject. The nutritional supplement was in capsular form, with a capsule including 300 mg artichoke extract standardized to 5% cynarin, ~4/3 mg forskolin, 167 mg L-phenylalanine, 5/3 mg vitamin B6, and 250 mg acetyl-L-carnitine. Also included were cellulose, vegetable stearate and silica as carriers. After taking the nutritional supplement, the subject reported increased focus and mental vision.

Example 7

This example is based on a testimonial by a male subject. The nutritional supplement was in capsular form, with a capsule including 300 mg artichoke extract standardized to 5% cynarin, ~4/3 mg forskolin, 167 mg L-phenylalanine, 5/3 mg vitamin B6, and 250 mg acetyl-L-carnitine. Also included were cellulose, vegetable stearate and silica as carriers. After taking the nutritional supplement, the subject reported increased focus and concentration.

Example 8

The inventor ingested 25 mg kanna extract (Zembrin®, Organic African Red Tea Imports, Los Angeles, Calif.), 1500 mg L-phenylalanine, and 4 mg forskolin (Better Body Sports LLC, Ventura, Calif.). This combination was administered once per morning After taking the combination, the inventor obtained much better scores on "Polygons" and "Odd One Out" tests (Cambridge Brain Sciences, Ontario, Canada). Studying was much easier and more enjoyable.

REFERENCES

The following publications are incorporated by reference herein:

1. Rutten K, Van donkelaar E L, Ferrington L, et al. Phosphodiesterase inhibitors enhance object memory independent of cerebral blood flow and glucose utilization in rats. Neuropsychopharmacology. 2009; 34(8):1914-25. PMID 19262466.
2. Egawa T, Mishima K, Matsumoto Y, Iwasaki K, Iwasaki K, Fujiwara M. Rolipram and its optical isomers, phosphodiesterase 4 inhibitors, attenuated the scopolamine-induced impairments of learning and memory in rats. Jpn J Pharmacol. 1997; 75(3):275-81. PMID 9434259.
3. Zhang H T, O'donnell J M. Effects of rolipram on scopolamine-induced impairment of working and reference memory in the radial-arm maze tests in rats. Psychopharmacology (Berl). 2000; 150(3):311-6. PMID 10923759.
4. Zhang H T, Crissman A M, Dorairaj N R, Chandler L J, O'donnell J M Inhibition of cyclic AMP phosphodiesterase (PDE4) reverses memory deficits associated with NMDA receptor antagonism. Neuropsychopharmacology. 2000; 23(2):198-204. PMID 10882846.
5. Zhang H T, Huang Y, Suvarna N U, et al. Effects of the novel PDE4 inhibitors MEM1018 and MEM1091 on memory in the radial-arm maze and inhibitory avoidance tests in rats. Psychopharmacology (Berl). 2005; 179(3): 613-9. PMID 15672274.
6. Mclean J H, Smith A, Rogers S, Clarke K, Darby-king A, Harley C W. A phosphodiesterase inhibitor, cilomilast, enhances cAMP activity to restore conditioned odor preference memory after serotonergic depletion in the neonate rat. Neurobiol Learn Mem. 2009; 92(1):63-9. PMID 19233302.
7. Wang C, Yang X M, Zhuo Y Y, et al. The phosphodiesterase-4 inhibitor rolipram reverses Aβ-induced cognitive impairment and neuroinflammatory and apoptotic responses in rats. Int J Neuropsychopharmacol. 2012; 15(6):749-66. PMID 21733236.
8. Rose G M, Hopper A, De vivo M, Tehim A. Phosphodiesterase inhibitors for cognitive enhancement. Curr Pharm Des. 2005; 11(26):3329-34. PMID 16250839.
9. Drott J, Desire L, Drouin D, Pando M, Haun F. Etazolate improves performance in a foraging and homing task in aged rats. Eur J Pharmacol. 2010; 634(1-3):95-100. PMID 20223232.
10. Li L X, Cheng Y F, Lin H B, Wang C, Xu J P, Zhang H T. Prevention of cerebral ischemia-induced memory deficits by inhibition of phosphodiesterase-4 in rats. Metab Brain Dis. 2011; 26(1):37-47. PMID 21327879.
11. Gallant M, Aspiotis R, Day S, et al. Discovery of MK-0952, a selective PDE4 inhibitor for the treatment of long-term memory loss and mild cognitive impairment. Bioorg Med Chem Lett. 2010; 20(22):6387-93. PMID 20933411.
12. Heaslip R J, Evans D Y. Emetic, central nervous system, and pulmonary activities of rolipram in the dog. Eur J Pharmacol. 1995; 286(3):281-90. PMID 8608790.
13. Bruno O, Fedele E, Prickaerts J, et al. GEBR-7b, a novel PDE4D selective inhibitor that improves memory in rodents at non-emetic doses. Br J Pharmacol. 2011; 164 (8):2054-63. PMID 21649644.

14. Mackenzie S J, Houslay M D. Action of rolipram on specific PDE4 cAMP phosphodiesterase isoforms and on the phosphorylation of cAMP-response-element-binding protein (CREB) and p38 mitogen-activated protein (MAP) kinase in U937 monocytic cells. Biochem J. 2000; 347(Pt 2):571-8. 10749688.
15. Xu W, Kasper L H, Lerach S, Jeevan T, Brindle P K. Individual CREB-target genes dictate usage of distinct cAMP-responsive coactivation mechanisms. EMBO J. 2007; 26(12):2890-903. PMID 17525731.
16. Benito E, Valor L M, Jimenez-minchan M, Huber W, Barco A. cAMP response element-binding protein is a primary hub of activity-driven neuronal gene expression. J Neurosci. 2011; 31(50):18237-50. PMID 22171029.
17. Lee J, Kim C H, Simon D K, et al. Mitochondrial cyclic AMP response element-binding protein (CREB) mediates mitochondrial gene expression and neuronal survival. J Biol Chem. 2005; 280(49):40398-401. PMID 16207717.
18. Deisseroth K, Bito H, Tsien R W. Signaling from synapse to nucleus: postsynaptic CREB phosphorylation during multiple forms of hippocampal synaptic plasticity. Neuron. 1996; 16(1):89-101. PMID 8562094.
19. Kida S. A Functional Role for CREB as a Positive Regulator of Memory Formation and LTP. Exp Neurobiol. 2012; 21(4):136-40. PMID 23319873.
20. Suzuki A, Fukushima H, Mukawa T, et al. Upregulation of CREB-mediated transcription enhances both short- and long-term memory. J Neurosci. 2011; 31(24):8786-802. PMID 21677163.
21. Ammon H P, Müller A B. Forskolin: from an ayurvedic remedy to a modern agent. Planta Med. 1985; 51(6):473-7. PMID 17345261.
22. Seamon K B, Daly J W. Forskolin: a unique diterpene activator of cyclic AMP-generating systems. J Cyclic Nucleotide Res. 1981; 7(4):201-24. PMID 6278005.
23. Barad M, Bourtchouladze R, Winder D G, Golan H, Kandel E. Rolipram, a type IV-specific phosphodiesterase inhibitor, facilitates the establishment of long-lasting long-term potentiation and improves memory. Proc Natl Acad Sci USA. 1998; 95(25):15020-5. PMID 9844008.
24. Brown J E, Rice-evans C A. Luteolin-rich artichoke extract protects low density lipoprotein from oxidation in vitro. Free Radic Res. 1998; 29(3):247-55. PMID 9802556.
25. Yu M C, Chen J H, Lai C Y, Han C Y, Ko W C. Luteolin, a non-selective competitive inhibitor of phosphodiesterases 1-5, displaced [3H]-rolipram from high-affinity rolipram binding sites and reversed xylazine/ketamine-induced anesthesia. Eur J Pharmacol. 2010; 627(1-3):269-75. PMID 19853596.
26. Kitagawa Y, Hirano T, Kawaguchi S Y. Prediction and validation of a mechanism to control the threshold for inhibitory synaptic plasticity. Mol Syst Biol. 2009; 5:280. PMID 19536203.
27. Puzzo D, Sapienza S, Arancio O, Palmeri A. Role of phosphodiesterase 5 in synaptic plasticity and memory. Neuropsychiatr Dis Treat. 2008; 4(2):371-87. PMID 18728748.
28. Otmakhov N, Khibnik L, Otmakhova N, et al. Forskolin-induced LTP in the CA1 hippocampal region is NMDA receptor dependent. J Neurophysiol. 2004; 91(5):1955-62. PMID 14702333.
29. Piech-dumas K M, Tank A W. CREB mediates the cAMP-responsiveness of the tyrosine hydroxylase gene: use of an antisense RNA strategy to produce CREB-deficient PC12 cell lines. Brain Res Mol Brain Res. 1999; 70(2):219-30. PMID 10407170.
30. Kumer S C, Vrana K E. Intricate regulation of tyrosine hydroxylase activity and gene expression. J Neurochem. 1996; 67(2):443-62. PMID 8764568.
31. Slominski A, Zmijewski M A, Pawelek J. L-tyrosine and L-dihydroxyphenylalanine as hormone-like regulators of melanocyte functions. Pigment Cell Melanoma Res. 2012; 25(1):14-27. PMID 21834848.
32. Amadasi A, Bertoldi M, Contestabile R, et al. Pyridoxal 5'-phosphate enzymes as targets for therapeutic agents. Curr Med Chem. 2007; 14(12):1291-324. PMID 17504214.
33. Curtin B F, Pal N, Gordon R K, Nambiar M P. Forskolin, an inducer of cAMP, up-regulates acetylcholinesterase expression and protects against organophosphate exposure in neuro 2A cells. Mol Cell Biochem. 2006; 290(1-2):23-32. PMID 16924422.
34. Hartvig P, Lindström B, Pettersson E, Wiklund L. Reversal of postoperative somnolence using a two-rate infusion of physostigmine. Acta Anaesthesiol Scand. 1989; 33(8):681-5. PMID 2589000.
35. White H L, Scates P W. Acetyl-L-carnitine as a precursor of acetylcholine. Neurochem Res. 1990; 15(6):597-601. PMID 2215852.
36. Alasbahi R H, Melzig M F. (2012) "Forskolin and derivatives as tools for studying the role of cAMP." Pharmazie. 2012 January; 67(1):5-13. PMID: 22393824.
37. Yu M C, Chen J H, Lai C Y, Han C Y, Ko W C. (2010) "Luteolin, a non-selective competitive inhibitor of phosphodiesterases 1-5,displaced [3H]-rolipram from high-affinity rolipram binding sites and reversed xylazine/ketamine-induced anesthesia." Eur J Pharmacol. 2010 Feb. 10; 627(1-3):269-75. doi: 10.1016/j.ejphar.2009.10.031. Epub 2009 Oct. 22 PMID: 19853596.
38. Harvey A L, Young L C, Viljoen A M, Gericke N P. (2011) "Pharmacological actions of the South African medicinal and functional food plant *Sceletium tortuosum* and its principal alkaloids." J Ethnopharmacol. 2011 Oct. 11; 137(3):1124 9. doi: 10.1016/j.jep.2011.07.035. Epub 2011 Jul. 20. PMID: 21798331.
39. Dwight E. Matthews (2008) "An Overview of Phenylalanine and Tyrosine Kinetics in Humans" J Nutr. Author manuscript; available in PMC 2008 Mar. 17. Published in final edited form as: J Nutr. 2007 June; 137(6 Suppi 1):1549S-1575S.PMCID: PMC2268015.
40. Lichtstein H C, Gunsalus I C, Umbreit W W (1945). "Function of the vitamin B6 group; pyridoxal phosphate (codecarboxylase) in transamination" (PDF). J Bioi Chem. 161 (1): 311-20.PMID 21005738.
41. Rani P J, Panneerselvam C. (2001). "Protective efficacy of L-carnitine on acetylcholinesterase activity in aged rat brain." J Gerontal A Bioi Sci Med Sci. 2001 March; 56(3):B140-1.PMID: 11253151.
42. Villa R F, Ferrari F, Gorini A. (2013) "ATP-ases of synaptic plasma membranes in striatum: Enzymatic systems for synapses functionality by in vivo administration of 1-acetylcarnitine in relation to Parkinson's Disease." Neuroscience. 2013 Jun. 25; 248C:414-426. doi: 10.1016/j.neuroscience.2013.06.027. [Epub ahead of print] PMID: 23806723.
43. Curtin B F, Pal N, Gordon R K, Nambiar M P. (2006). "Forskolin, an inducer of cAMP, upregulates acetylcholinesterase expression and protects against organophosphate exposure in neuro 2A cells" Mol Cell Biochem. 2006 October; 290(1-2):23-32. Epub 2006 Aug. 19. PMID 16924422.
44. Gong B, Vitolo O V, Trinchese F, Liu S, Shelanski M, Arancio O., (2004) "Persistent improvement in synaptic and cognitive functions in an Alzheimer mouse model after rolipram treatment." J Clin Invest. 2004 December; 114(11):1624-34. PMID: 15578094.
45. Voisin P, Bernard M. (2013) "Cyclic AMP-dependent regulation of tyrosine hydroxylase mRNA and immunofluorescence levels in rat retinal precursor cells." Cell Tissue Res. 2013 May; 352(2):207-16. doi: 10.1007/s00441-013-1555-4. Epub 2013 Jan. 26. PMID: 2335501.
46. Chan A L, Huang H L, Chien H C, Chen C M, Lin C N, Ko W C Inhibitory effects of quercetin derivatives on phosphodiesterase isozymes and high-affinity [(3) H]-rolipram binding in guinea pig tissues. Invest New Drugs. 2008; 26(5):417-24. PMID 18264679.
47. Yang Y L, Hsu H T, Wang K H, Wang C S, Chen C M, Ko W C. Hesperidin-3'-o-methylether is more potent than hesperidin in phosphodiesterase inhibition and suppression of ovalbumin-induced airway hyperresponsiveness. Evid Based Complement Alternat Med. 2012; 2012: 908562. PMID 23082087.
48. Park S J, Ahmad F, Philp A, et al. Resveratrol ameliorates aging-related metabolic phenotypes by inhibiting cAMP phosphodiesterases. Cell. 2012; 148(3):421-33. PMID 22304913.
49. Ko W C, Lin L H, Shen H Y, Lai C Y, Chen C M, Shih C H. Biochanin a, a phytoestrogenic isoflavone with selective inhibition of phosphodiesterase 4, suppresses ovalbumin-induced airway hyperresponsiveness. Evid Based Complement Alternat Med. 2011; 2011:635058. PMID 21437195.
50. Nichols M R, Morimoto B H. Tyrosine kinase-independent inhibition of cyclic-AMP phosphodiesterase by genistein and tyrphostin 51. Arch Biochem Biophys. 1999; 366(2):224-30. PMID 10356287.
51. Harvey A L, Young L C, Viljoen A M, Gericke N P. Pharmacological actions of the South African medicinal and functional food plant *Sceletium tortuosum* and its principal alkaloids. J Ethnopharmacol. 2011; 137(3): 1124-9. PMID 21798331.
52. Shoba G, Joy D, Joseph T, Majeed M, Rajendran R, Srinivas P S. Influence of piperine on the pharmacokinetics of curcumin in animals and human volunteers. Planta Med. 1998; 64(4):353-6. PMID 9619120.
53. Johnson J J, Nihal M, Siddiqui 1A, et al. Enhancing the bioavailability of resveratrol by combining it with piperine. Mol Nutr Food Res. 2011; 55(8):1169-76. PMID 21714124.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the invention and the following claims.

What is claimed is:

1. A nootropic combination for increasing cognitive functioning in a human subject, comprising effective amounts of a phosphodiesterase 4 (PDE4) inhibitor and a cyclic adenosine monophosphate (cAMP) increasing agent,
    wherein the PDE4 inhibitor is luteolin, quercetin, hesperidin, biochanin A, genistein, mesembrenone, or resveratrol, or a glycoside thereof, a physiologically acceptable salt thereof, or a combination thereof, and the cAMP increasing agent is forskolin in a range of about 0.9 mg to about 4.4 mg per daily dose of the combination.

2. The nootropic combination of claim 1, further comprising an effective amount of acetyl-L-carnitine or a physiologically acceptable salt thereof.

3. The nootropic combination of claim 1, further comprising an effective amount of acetyl-L-carnitine, and wherein the ratio of acetyl-L-carnitine to forskolin is about 200:1 by weight.

4. The nootropic combination of claim 1, further comprising effective amounts of one or a combination of components selected from the group consisting of L-phenylalanine, L-carnitine, acetyl-L-carnitine, vitamin B6, piperine, and a physiologically acceptable salt thereof.

5. The nootropic combination of claim 1, further comprising an effective amount of acetyl-L-carnitine.

6. The nootropic combination of claim 1, further comprising an effective amount of piperine.

7. The nootropic combination of claim 1, further comprising an effective amount of L-phenylalanine.

8. The nootropic combination of claim 1, further comprising an effective amount of vitamin B6.

9. The nootropic combination of claim 1, wherein the PDE4 inhibitor, the cAMP increasing agent, or both, are present in the combination in the form of one or more plant extracts.

10. The nootropic combination of claim 1, in the form of a nutritional supplement, further comprising an effective amount of acetyl-L-carnitine, and wherein the PDE4 inhibitor is present in the nutritional supplement in the form of a plant extract.

11. The nootropic combination of claim 10, wherein the ratio of acetyl-L-carnitine to forskolin is about 200:1 by weight.

12. The nootropic combination of claim 10, wherein the forskolin is present in the nutritional supplement in the form of *Coleus forskohlii* extract.

13. The nootropic combination of claim 10, wherein the forskolin is present in the nutritional supplement in the form of a *Coleus forskohlii* extract, and the ratio of acetyl-L-carnitine to forskolin is about 200:1 by weight.

14. The nootropic combination of claim 10, further comprising effective amounts of one or any combination of components selected from the group consisting of L-phenylalanine, L-carnitine, vitamin B6, and piperine.

15. The nootropic combination of claim 10, further comprising an effective amount of piperine.

16. The nootropic combination of claim 10, further comprising an effective amount of L-phenylalanine.

17. The nootropic combination of claim 10, further comprising an effective amount of vitamin B6.

18. A nootropic combination, in the form of a nutritional supplement, comprising in daily dosage form:
    about 202.5 mg to about 990 mg of artichoke extract standardized to 5% cynarin, as a source of a PDE4 inhibitor, per about 0.9 mg to about 4.4 mg of forskolin; and
    about 180 mg to about 880 mg of acetyl-L-carnitine per about 0.9 mg to about 4.4 mg of forskolin.

19. The nootropic combination of claim 18, further comprising one or any combination of components selected from the group consisting of about 112.5 mg to about 550 mg of L-phenylalanine per daily dosage of the nutritional supplement, about 2.25 mg to about 11 mg of vitamin B6 per daily dosage of the nutritional supplement, and about 10 mg to about 20 mg of piperine per daily dosage of the nutritional supplement.

20. The nootropic combination of claim 18, wherein the ratio of acetyl-L-carnitine to forskolin is about 200:1 by weight.

21. The nootropic combination of claim 18, further comprising:
- about 112.5 mg to about 550 mg of L-phenylalanine per daily dosage of the nutritional supplement; and
- about 2.25 mg to about 11 mg of vitamin B6 per daily dosage of the nutritional supplement.

22. The nootropic combination of claim 18, in capsule form, comprising per capsule:
- about 300 mg of artichoke extract standardized to 5% cynarin;
- about 4/3 mg of forskolin;
- about 250 mg of acetyl-L-carnitine;
- about 500/3 mg of L-phenylalanine; and
- about 5/3 mg vitamin B6.

23. A method of increasing cognitive functioning in a human subject in need thereof, comprising administering to the subject a daily dose of a nutritional supplement that comprises effective amounts of a cyclic adenosine monophosphate (cAMP) increasing agent and a PDE4 inhibitor,
wherein the PDE4 inhibitor is luteolin, quercetin, hesperidin, biochanin A, genistein, mesembrenone, or resveratrol, or a glycoside thereof, a physiologically acceptable salt thereof, or a combination thereof, and
the cAMP increasing agent is forskolin in a range of about 0.9 mg to about 4.4 mg per daily dose of the nutritional supplement.

24. The method of claim 23, further comprising an effective amount of acetyl-L-carnitine or a physiologically acceptable salt thereof.

25. The method of claim 23, further comprising an effective amount of acetyl-L-carnitine and wherein the ratio of acetyl-L-carnitine to forskolin is about 200:1 by weight.

26. The method of claim 23, wherein the forskolin is present in the nutritional supplement in the form of a *Coleus forskohlii* extract.

27. The method of claim 23, wherein the PDE4 inhibitor, the cyclic cAMP increasing agent, or both, are present in the nutritional supplement in the form of one or more plant extracts.

28. The method of claim 23, wherein the nutritional supplement further comprises therapeutically effective amounts of one or any combination of components selected from the group consisting of L-phenylalanine, L-carnitine, acetyl-L-carnitine, vitamin B6, piperine, and a physiologically acceptable salt thereof.

29. The method of claim 23, wherein the nutritional supplement further comprises an effective amount of piperine.

30. The nutritional supplement of claim 23, wherein the nutritional supplement further comprises an effective amount of L-phenylalanine.

31. The nutritional supplement of claim 23, wherein the nutritional supplement further comprises an effective amount of vitamin B6.

32. The method of claim 23, wherein the nutritional supplement comprises, in daily dosage form:
- about 202.5 mg to about 990 mg of artichoke extract standardized to 5% cynarin, as a source of the PDE4 inhibitor, per about 0.9 mg to about 4.4 mg of forskolin; and
- further includes about 180 mg to about 880 mg of acetyl-L-carnitine about 0.9 mg to about 4.4 mg of forskolin.

33. The method of claim 32, wherein the nutritional supplement further comprises one or any combination of components selected from the group consisting of about 112.5 mg to about 550 mg of L-phenylalanine per daily dosage of the nutritional supplement, about 2.25 mg to about 11 mg of vitamin B6 per daily dosage of the nutritional supplement, and about 10 mg to about 20 mg of piperine per daily dosage of the nutritional supplement.

34. The method of claim 32, wherein the ratio of acetyl-L-carnitine to forskolin is about 200:1 by weight.

35. The method of claim 32, wherein the nutritional supplement further comprises:
- about 112.5 mg to about 550 mg of L-phenylalanine per daily dosage of the nutritional supplement; and
- about 2.25 mg to about 11 mg of vitamin B6 per daily dosage of the nutritional supplement.

36. The method of claim 23, wherein the subject is administered two or three capsules of the nutritional supplement, per daily dosage, wherein each capsule comprises:
- about 300 mg of artichoke extract standardized to 5% cynarin;
- about 4/3 mg of forskolin;
- about 250 mg of acetyl-L-carnitine;
- about 500/3 mg of L-phenylalanine; and
- about 5/3 mg vitamin B6.

* * * * *